United States Patent [19]

Sprecker et al.

[11] Patent Number: 4,791,222

[45] Date of Patent: Dec. 13, 1988

[54] PROCESS FOR PREPARING DIHYDROMYRCENOL AND DIHYDROMYRCENYL ACETATE

[75] Inventors: Mark A. Sprecker, Sea Bright, N.J.; Stephen R. Wilson, Haverhill, United Kingdom; Leonard Steinbach, Cranford; Thomas O'Rourke, Red Bank, both of N.J.

[73] Assignee: International Flavors & Fragrances Inc., New York, N.Y.

[21] Appl. No.: 636,326

[22] Filed: Jul. 31, 1984

[51] Int. Cl.$^4$ .................. C07C 69/145; C07C 67/11; C07C 33/025; C07C 29/124
[52] U.S. Cl. .................................. 560/237; 560/249; 560/261; 568/875; 568/892; 568/893
[58] Field of Search .................... 560/237, 261, 249; 568/892, 875, 893

[56] References Cited

U.S. PATENT DOCUMENTS 2,902,495 9/1959 Webb .................................. 560/263
2,902,510 9/1959 Webb .................................. 560/249

OTHER PUBLICATIONS

Anandaraman, et al., Tetrahedron Letters, vol. 21, pp. 2189–2190 (1980).
Gurudutt, et al., Tetrahedron Letters, vol. 38, No. 12, pp. 1843–1846, (1982).

*Primary Examiner*—Vivian Garner
*Attorney, Agent, or Firm*—Arthur L. Liberman

[57] ABSTRACT

Described is a novel process for preparing dihydromyrcenol defined according to the structure:

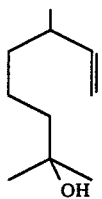

or the acetate thereof comprising the steps of:
(i) hydrogenating α-pinene to form α-pinane;
(ii) pyrolizing the resulting α-pinane to form a mixture of hydrocarbons including dihydromyrcene (or, in the alternative, forming substantially the same mixture of hydrocarbons by other well known means);
(iii) reacting the resulting pinane pyrolyzate or like mixture with hydrogen chloride gas in the presence of an acid catalyst, e.g., Lewis acid or protonic acid, to form a mixture of tertiary chlorides; then
(iv) reacting the mixture of tertiary chlorides with water or acetic acid in the presence of a hydroxylation catalyst defined according to the formula:

$$M_P X_Q$$

wherein M represents an element selected from the group consisting of Zn, Ca, Mg, Mn and Co; wherein X represents O or an anion, e.g., halide hydroxide, carbonate, bicarbonate, phosphate, monobasic acid phosphate or dibasic acid phosphate; and wherein P represents an integer of 1 or 3 and Q represents an interger of 1 or 2, with the provisos that when X is a trivalent anion, then p is 3 and Q is 2 and when X is a divalent anion or is O, the P is 1 and Q is 1 and when X is a monovalent anion, then P is 1 and Q is 2; and
(v) recovering the dihydromyrcenol or acetate thereof from the reaction product where the dihydromyrcenol or acetate thereof is produced in relatively high yields.

4 Claims, 3 Drawing Sheets

GLC PROFILE FOR EXAMPLE I.
REACTANT

FIG. 4

GLC PROFILE FOR EXAMPLE IV.

FIG. 3

GLC PROFILE FOR EXAMPLE II(B). CRUDE

PROCESS FOR PREPARING DIHYDROMYRCENOL AND DIHYDROMYRCENYL ACETATE

BACKGROUND OF THE INVENTION

Dihydromyrcenol defined according to the structure:

was heretofore produced commercially by means of:
(i) hydrogenating α-pinene to form α-pinane;
(ii) pyrolyzing the α-pinene to form α-pinane pyrolyzate containing a mixture of hydrocarbons;
(iii) carefully distilling the resulting α-pinane pyrolyzate in order to obtain dihydromyrcene of a very high purity, dihydromyrcene having the structure:

(iv) reacting the dihydromyrcene with hydrogen chloride in order to form dihydromyrcenyl chloride defined according to the structure:

and then
(v) hydroxylating the resulting dihydromyrcenyl chloride to form dihydromyrcenol having the structure:

Thus, U.S. Pat. No. 2,902,510, at Example VIII discloses the reaction of dihydromyrcene with hydrogen chloride gas in order to form, in 95–98% yields, dihydromyrcenyl chloride according to the reaction:

In Example IX of U.S. Pat. No. 2,902,510 the resulting dihydromyrcenyl chloride is reacted with water, in the presence of calcium hydroxide in order to form, in 65–70% yields, dihydromyrcenol according to the reaction:

The reaction of tertiary terpenyl halides with water to form tertiary terpenols, specifically α-terpeneol is disclosed in Anandaraman, et al, Tetrahedron Letters, Vol. 21, pages 2189–2190, (1980) and in Gurudutt, et al, Tetrahedron, Vol. 38, No. 12, pages 1843–1846.

Thus, Anandaraman, et al, discloses the reactions:

and

-continued and indicates that the attempted reaction of a secondary halide to form its corresponding alcohol does not take place when using zinc salts or zinc oxide as hydroxylation catalysts, to wit:

Gurudutt, et al, indicates that the following reaction can take place:

Furthermore, a technique for formation of the α-pinane pyrolyzate is set forth in U.S. Pat. No. 2,902,495 issued on Sept. 1, 1959, the specification for which is incorporated by reference herein.

Nothing in the prior art, however, indicates that the entire α-pinane pyrolyzate or a mixture containing the components thereof produced in any other manner:

(i) can first be hydrohalogenated in the presence of an acid catalyst, e.g., a Lewis acid or protonic acid catalyst; and then (ii) the resulting mixture of tertiary halides can be, en masse, hydroxylated with water or acetoxylated with acetic acid using one or more of a specific group of hydroxylation or of acetoxylation catalysts whereby the only tertiary alcohol (or acetate thereof) formed is dihydromyrcenol (or its acetate) and whereby other materials which are formed are merely hydrocarbons which can easily, economically and quickly be separated from said dihydromyrcenol (or its acetate).

BRIEF DESCRIPTION OF THE DRAWINGS

FIG. 3 is the GLC profile for the crude reaction product of Example II containing a high proportion of dihydromyrcenol defined according to the structure:

as well as a number of hydrocarbons hereinafter specifically described.

SUMMARY OF THE INVENTION

The instant invention takes advantage of the unexpected discovery that:

(i) α-pinane pyrolyzate (or substantially the same mixture of hydrocarbons formed by any other known means) can first be hydrochlorinated to form a mixture of tertiary chlorides defined according to the structures:

and (ii) the resulting mixture of tertiary chlorides can be treated with water or acetic acid in the presence of a hydroxylating catalyst having the formula:

$M_pX_q$ wherein M represents an element selected from the group consisting of Zn, Ca, Mg, Mn and Co; wherein X represents O or an anion, e.g., halide, hydroxide, carbonate, bicarbonate, phosphate, monobasic acid phosphate or dibasic acid phosphate; and wherein P represents an integer of 1 or 3 and Q represents an integer of 1 or 2 with the provisos that when X is a trivalent anion, then P is 3 and q is 2 and when X is a divalent anion or is 0, then P is 1 and Q is 1 and when X is a monovalent anion, then P is 1 and Q is 2; and (iii) the resulting dihydromyrcenol or its acetate can be distilled from the reaction product;

where (a) the dihydromyrcenol or its acetate is produced in relatively high yields (b) the only tertiary halide that is actually hydroxylated or acetoxylated is dihydromyrcenyl chloride defined according to the structure:

under the conditions of the reaction and (c) none of the other tertiary chlorides are hydroxylated or acetoxylated but instead are dehydrohalogenated to form the mixture of hydrocarbons defined according to the structure:

The resulting dihydromyrcenol having the structure:

(or its acetate) is easily separated by a very low-cost and highly efficient distillation from the hydrocarbon compounds having the structures:

Restated, the process of our invention consists of the steps of:

(i) first hydrogenating α-pinene to form α-pinane according to the reaction:

(ii) then pyrolyzing the α-pinane according to the reaction:

(or, in the alternative, forming substantially the same mixture of hydrocarbons by other well known means);

(iii) then hydrochlorinating the resulting α-pinane pyrolyzate (containing unreacted α-pinane) (or substantially the same mixture formed by other well known means) in the presence of an acid catalyst selected from the group consisting of protonic acids and Lewis acids according to the reaction:

(iv) then treating the resulting mixture of tertiary chlorides with water in the presence of a hydroxylating catalyst defined according to the formula:

$$M_p X_q$$

wherein M represents an element selected from the group consisting of Zn, Ca, Mg, Mn and Co; wherein X represents O or an anion, e.g., halide, hydroxide, carbonate, bicarbonate, phosphate, monobasic acid phosphate or dibasic acid phosphate; and wherein p represents an integer of 1 or 3 and Q represents an integer of 1 or 2 with the provisos that when X is a trivalent anion, then p is 3 and Q is 2 and when X is a divalent anion or is 0, then p is 1 and Q is 1 and when X is a monovalent anion, then p is 1 and Q is 2 according to the reaction:

H₂O + the temperature of reaction being between about 50° C. and about 100° C.; and

(iv) then fractionally distilling the resulting dihydromyrcenol having the structure:

from the reaction mass.

Figure 1:
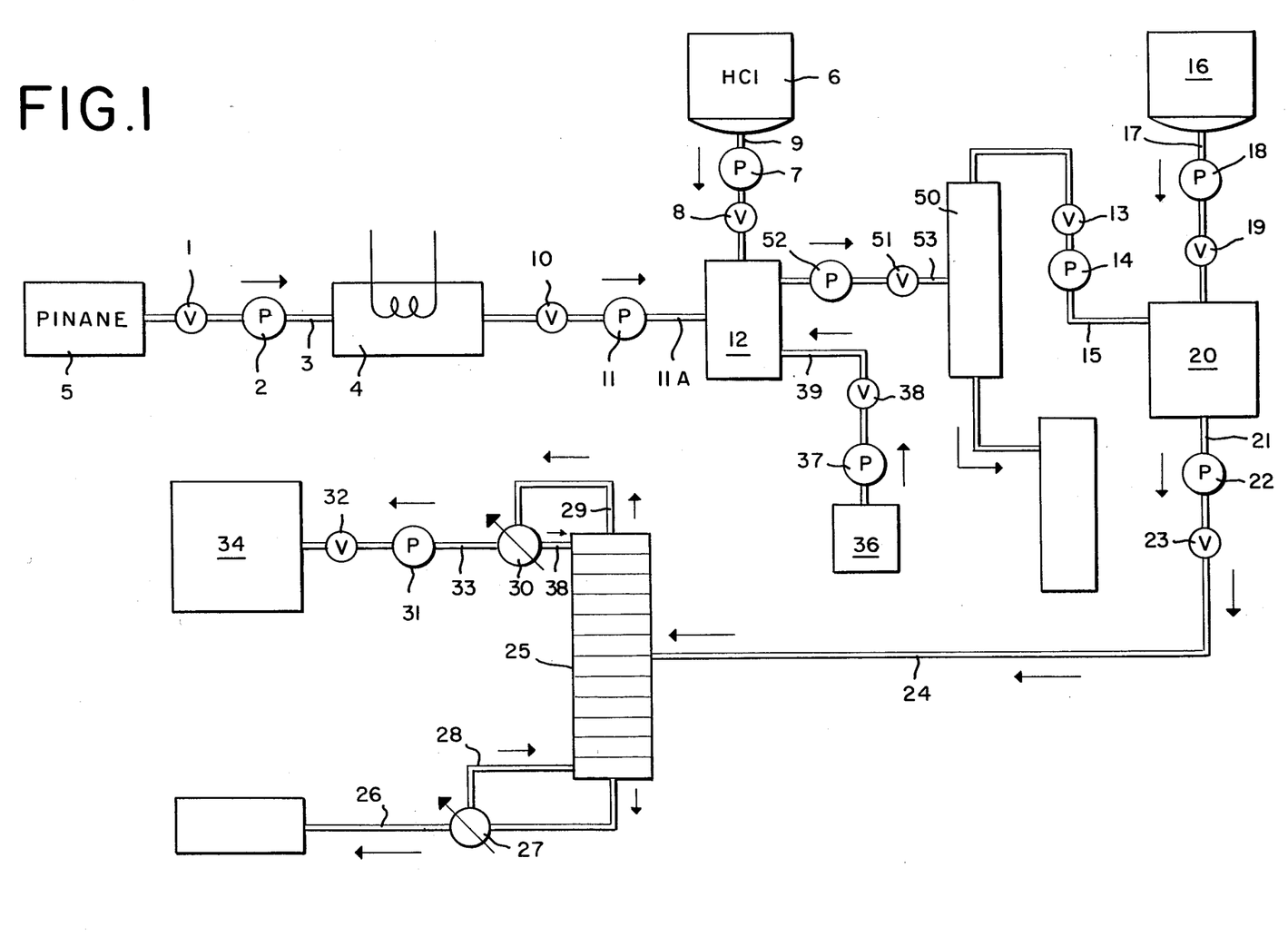
FIG. 1 is a schematic block flow diagram setting forth in schematic form a continuous process embodiment of our invention.

Another feature of our invention derived from the foregoing sequence of steps is to carry out the last reaction step using acetic acid (rather than water) as a reactant thereby forming dihydromyrcenyl acetate rather than the dihydromyrcenol according to the reaction:

is pyrolized according to Example II of U.S. Pat. No. 2,902,495 issued on Sept. 1, 1959 and repeated herein as Example I, infra, according to the reaction:

at a temperature of between 400° and 700° C.; preferably at a temperature of between 550° and 650° C. in the pyrolysis reactor 4 after the α-pinane in reservoir 5 is pumped through line 3 using pump 2 past valve 1. The resulting pyrolyzate including unreacted α-pinane having the structures:

rich in dihydromyrcene having the structure:

DETAILED DESCRIPTION OF THE INVENTION AND DRAWINGS

FIG. 1 is a schematic block flow diagram showing the steps of the process of our invention in schematic form. α-Pinane defined according to the structure:

produced by hydrogenation of α-pinene having the structure:

according to the reaction:

rather than being distilled according to the prior art is pumped through line 11A using pump 11 past valve 10 into hydrochlorination reactor 12. Into hydrochlorination reactor 12 is placed a catalyst selected from the group consisting of protonic acids and Lewis acids.

Examples of Lewis acids are boron trifluoride, boron trifluoride etherate, aluminum chloride, stannous chloride, zinc chloride, diethyl aluminum chloride, dialuminum ethyl chloride and zinc bromide. Examples of protonic acid catalysts are sulfuric acid, phosphoric acid, methane sulfonic acid, para-toluenesulfonic acid and xylenesulfonic acid. The hydrogen chloride gas is passed into the reactor 12 from holding pressure vessel 6 through line 9 using pump 7 and past valve 8. The hydrochlorination reaction takes place at a temperature in the range of between about 0° C. and about 80° C. over a time period in the range of from about 1 hour up to about 10 hours. After the hydrochlorination reaction, the reaction mass is mixed with water fed into tank 12 from tank 36 through line 39 using pump 37 past valve 38. The resulting reaction mass is then pumped through line 53 using pump 52 past valve 51 into separator 50 where the aqueous phase is separated from the organic phase. The organic phase is pumped through line 15 using pump 14 past valve 13 into reaction vessel 20 where it is reacted with water and then in the presence of a hydroxylation catalyst having the formula:

$$M_P X_Q$$

wherein M represents an element selected from the group consisting of Zn, Ca, Mg, Mn and Co; wherein X represents 0 or an anion, e.g., halide, hydroxide, carbonate, bicarbonate, phosphate, monobasic acid phosphate or dibasic acid phosphate; and wherein p represents an integer of 1 or 3 and q represents an integer of 1 or 2 with the provisos that when X is a trivalent anion, then P is 3 and Q is 2 and when X is a divalent anion or is 0, then P is 1 and Q is 1 and when X is a monovalent anion, then P is 1 and Q is 2 according to the reaction:

H₂O + at a temperature in the range of from about 50° C. up to about 100° C. The amount of catalyst defined according to the formula:

$$M_P X_Q$$

is in the range of from about 0.5 up to about 0.7 mole equivalents (based upon the total number of moles of tertiary chloride reactant). The amount of water in the reaction mass may vary from about 1 mole equivalent up to about 50 mole equivalents based on the moles of tertiary chloride reaction mass; that is, the compounds defined according to the structures:

-continued

; and  .

The resulting dihydromyrcenol is then easily distilled from the reaction mass.

Instead of water being admixed with the hydroxylating catalyst being fed from vessel 16 through line 17 using pump 18 through valve 19 into hydroxylating reaction vessel 20, a mixture of acetic acid and water can be fed from vessel 16 through line 17 past valve 19 using pump 18 into acetoxylating vessel 20 in view of the reaction taking place:

The reaction temperature range may be 25°–100° C.; preferably 25°–40° C.

At the end of the reaction, the reaction mass is then pumped through line 21 using pump 22 past valve 23, line 24, into distillation column 25 which is multiplate distillation column (preferably between 5 and 10 plates). The resulting product is then fractionally distilled and the dihydromyrcenol having the structure:

or its acetate having the structure:

is distilled using reflux cutter 30 and reflux lines 29 and 38. The dihydromyrcenol or its acetate then flows through 33 by means of pump 31 past valve 32 into holding tank 34 for ultimate packaging and marketing. Simultaneously, the bottoms of the distillation are reboiled through reboiler 27 and reboiling line 28 and the remainder of the bottom are sent through line 26 for ultimate processing as desired.

Figure 2:
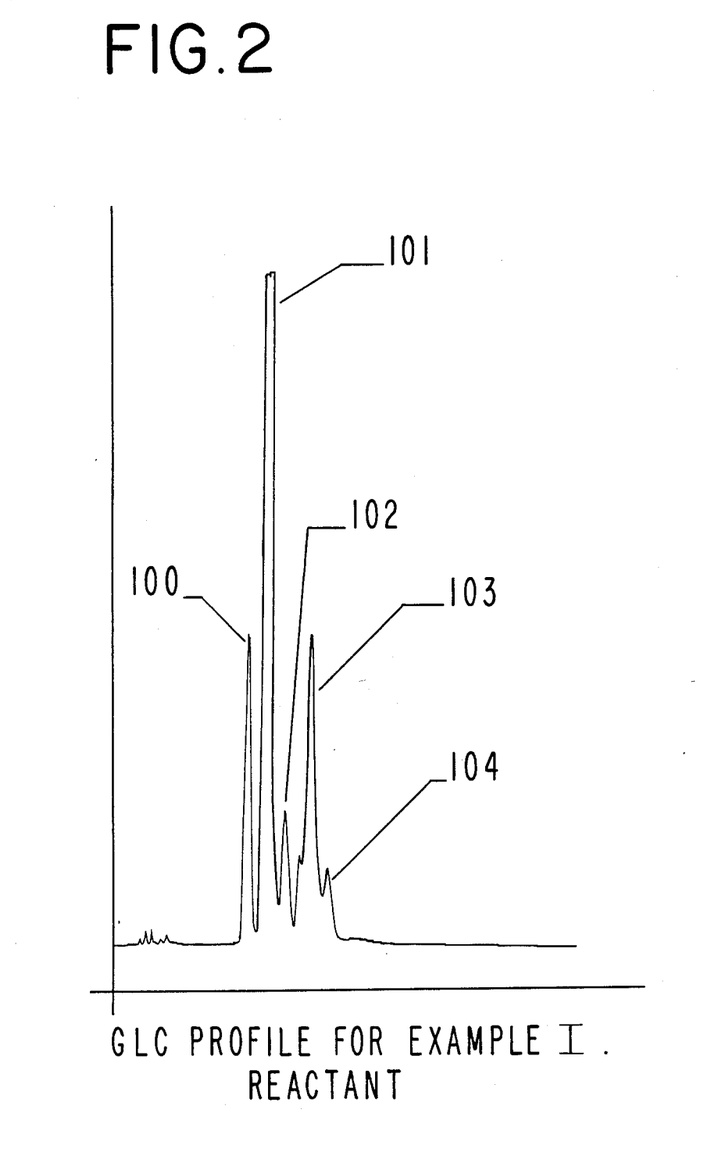
FIG. 2 is the GLC profile for the pinane pyrolyzate prepared in accordance with Example II of U.S. Pat. No. 2,902,495 issued on Sept. 1, 1959, used as a reactant in Example I, infra.

FIG. 2 is the GLC profile for the pinane pyrolyzate produced according to the process of Example I, infra and Example II of U.S. Pat. No. 2,902,495 issued on Sept. 1, 1959, and the specification for which is incorporated by reference herein and according to the reaction:

The peak indicated by reference numeral 100 is the peak for the compound having the structure:

The peak indicated by reference numeral 101 is the peak for dihydromyrcene having the structure:

The peak indicated by reference numeral 102 is the peak for the compound having the structure:

The peak indicated by reference numeral 103 is the peak for α-pinane having the structure:

The peak indicated by reference numeral 104 is the peak for the compound having the structure:

The conditions for the GLC profile are: SE-30 column programmed at 120° C. isothermal.

Figure 3:
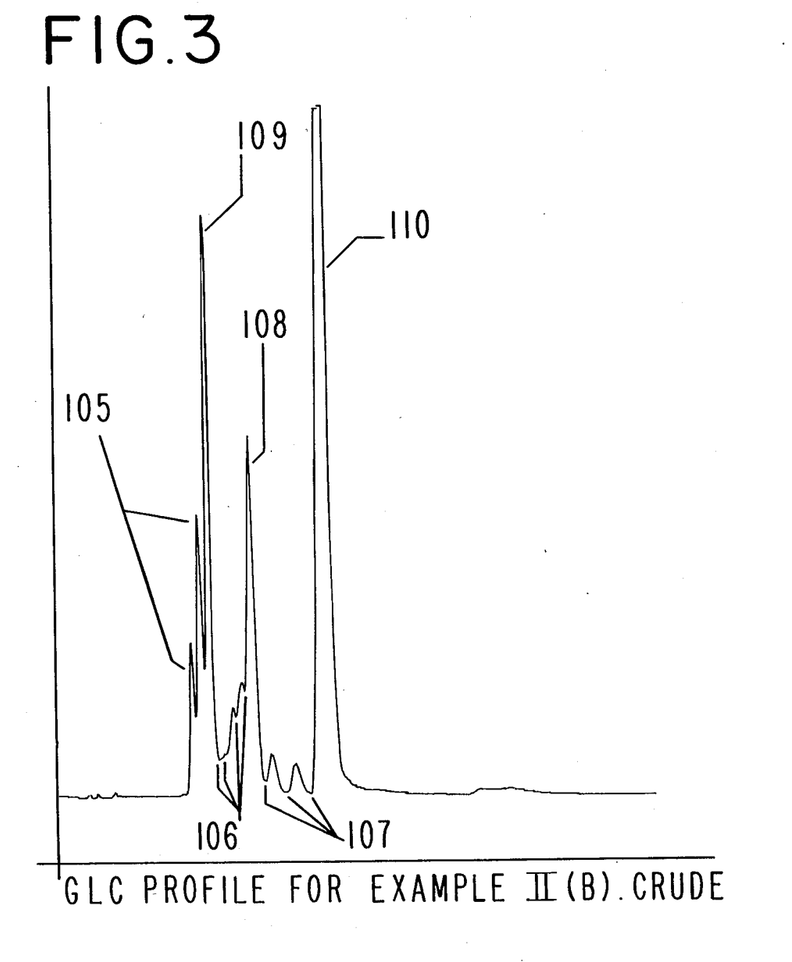

FIG. 3 is the GLC profile for the crude reaction product of Example II resulting from the reaction, to wit:

The peaks indicated by reference numeral 105 are peaks for the two compounds defined according to the structures:

The peaks indicated by reference numeral 106 are peaks for compounds having the structures:

The peaks indicated by reference numeral 107 are peaks for the compounds having the structures:

The peak indicated by reference numeral 108 is the peak for the α-pinane reactant contained in the reaction mixture and remaining unreacted having the structure:

The peak indicated by reference numeral 109 is the peak for the compound having the structure:

The peak indicated by reference numeral 110 is the peak for the dominant product in the reaction mixture, dihydromyrcenol having the structure:

The conditions for the GLC analysis are: SE-30 column programmed at 120° C. isothermal.

The primary utility of the dihydromyrcenol having the structure:

is for augmenting enhancing or imparting aroma in or to perfume compositions, colognes and perfumed articles including anionic, cationic, nonionic and zwitterionic detergents, fabric softener compositions, fabric softener articles, hair preparations, cosmetic powders, and perfumed polymers.

Figure 4:
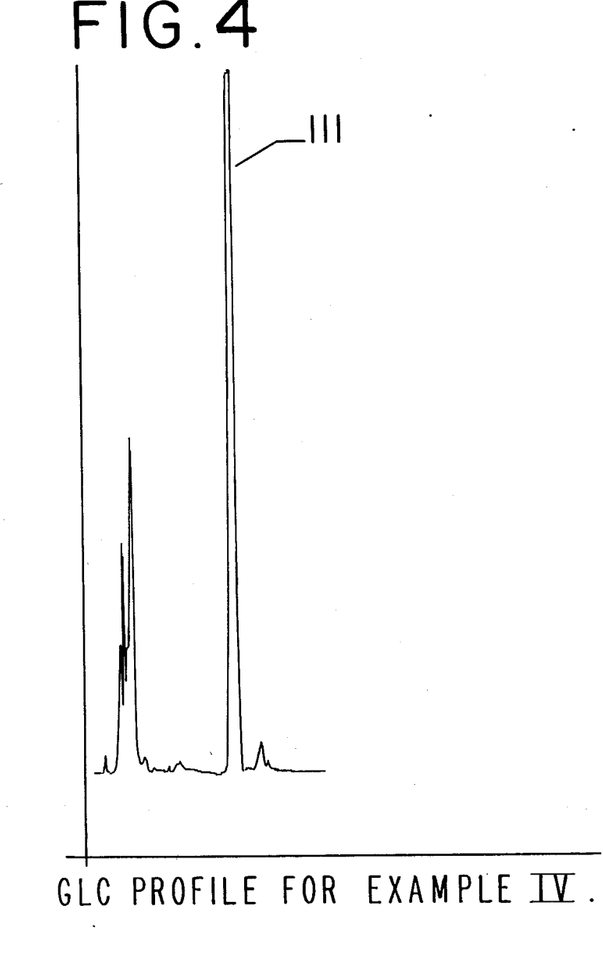
FIG. 4 is the GLC profile of the distillation of the reaction product of Example IV containing a high proportion of dihydromyrcenyl acetate defined according to the structure.

FIG. 4 is the GLC profile for the crude reaction product of Example IV wherein the reaction:

takes place. The peak indicated by reference numeral 111 is the peak for the compound having the structure:

(Conditions: Carbowax column programmed from 120° up to 220° C. at 32° C. per minute).

The following Examples serve to illustrate our invention and this invention is to be considered restricted thereto only as indicated in the appended claims.

All parts and percentages given herein are by weight unless otherwise specified.

EXAMPLE I

Hydrogenation of α-Pinene and Pyrolysis of Resulting α-Pinane

Reactions:

and

1000 Grams of α-pinene was hydrogenated in the presence of 1.0% by weight of a commercial nickel catalyst, (nickel content, 25%) at 100°–200° C. under a hydrogenation pressure of 50–80 psig. 1 Mole of hydrogen was added for each mole of α-pinene. The hydrogenation product was filtered to remove catalyst and fractionated through an efficient column at 100 mm/Hg. vacuum and 100° C.

The resulting pinane, bp 100° C. at 100 mm/Hg. vacuum, refractive index at 25° C.: 1.4607; specific gravity at 25° C.: 08541; $\alpha - d^{25}$ (10 cm) = 19.24° C. was then vaporized and passed through a 0.5 inch copper tube at 600°–620° C. at a rate of 0.25 grams per minute of liquid condensate.

FIG. 2 is the GLC profile for the resulting pyrolyzate containing the compounds having the structures:

and

EXAMPLE II(A)

Hydrohalogenation of α-Pinane Pyrolyzate

Reaction:

Into a 5 liter reaction vessel equipped with stirrer, thermometer, reflux condenser and hydrogen chloride gas bubbler are placed 3000 grams of α-pinane pyrolyzate produced according to Example I and 60 grams of stannous chloride dihydrate. The mixture of pinane pyrolyzate and stannous chloride dihydrate is then heated with stirring to 40° C. While maintaining the reaction mass at 40° C., over a two hour period, anhydrous hydrogen chloride gas is added through the sparger to the reaction mass.

The reaction mass is then washed with water and the resulting organic phase is utilized in Example II(B) as follows:

EXAMPLE II(B)

Hydroxylation of Tertiary Chloride Mixture

Reaction:

Into a 5 liter reaction flask equipped with stirrer, thermometer, reflux condenser and heating mantle are placed the following materials:
Tertiary chloride reaction product produced according to Example II(A) ... 3671 grams
Water ... 2 liters
ZnO ... 700 grams.

The reaction mass is heated to reflux with stirring and maintained at reflux with stirring for a period of 4.5 hours. At the end of the 4.5 hour period, the reaction mass is cooled to room temperature and the organic phase is washed with 2 liters of water followed by 2 liters of 10% sodium chloride solution.

The resulting organic phase is then distilled on a 12" Goodloe column yielding the following fractions:

| FRACTION NO. | VAPOR TEMP. (°C.) | LIQUID TEMP. (°C.) | VACUUM mm/Hg. |
|---|---|---|---|
| 1 | 23/70 | 23/81 | 50/50 |
| 2 | 70 | 82 | 50 |
| 3 | 70 | 85 | 50 |
| 4 | 73 | 90 | 50 |
| 5 | 74 | 97 | 50 |
| 6 | 90 | 100 | 30 |
| 7 | 92 | 97 | 25 |
| 8 | 82 | 87 | 15 |
| 9 | 75 | 84 | 10 |
| 10 | 75 | 82 | 10 |
| 11 | 75 | 80 | 10 |
| 12 | 70 | 78 | 7 |
| 13 | 70 | 78 | 7 |
| 14 | 65 | 75 | 5 |
| 15 | 65 | 60 | 5 |
| 16 | 65 | 75 | 5 |

-continued

| FRACTION NO. | VAPOR TEMP. (°C.) | LIQUID TEMP. (°C.) | VACUUM mm/Hg. |
|---|---|---|---|
| 17 | 65 | 75 | 5 |
| 18 | 65 | 75 | 5 |
| 19 | 67 | 78 | 5 |
| 20 | 67 | 78 | 5 |
| 21 | 67 | 81 | 5 |
| 22 | 67 | 90 | 5 |
| 23 | 67 | 90 | 5 |
| 24 | 67 | 90 | 5 |
| 25 | 67 | 120 | 5 |
| 26 | 40 | 220 | 1 |

FIG. 3 is the GLC profile for the crude reaction product prior to distillation (Conditions: SE-30 column programmed at 120° C. isothermal). The peak indicated by reference numeral 110 is the peak for dihydromyrcenol having the structure:

EXAMPLE III

Determination of Operable Hydroxylation Catalysts

Reaction:

REACTION "A"

0.5 Moles of dihydromyrcenyl chloride (95 grams) is admixed with 80 ml water and 12 grams (0.3 moles) of magnesium oxide. The resulting reaction mass is refluxed for a period of 11 hours yielding a product containing 70% dihdromyrcenol having the structure:

REACTION "B"

0.5 Moles dihydromyrcenyl chloride (95 grams) is admixed with 80 ml water and 17 grams (0.3 moles) of calcium oxide. The reaction mass is refluxed for a period of 11 hours. The resulting reaction mass contains 41% by weight of dihydromyrcenol having the structure:

REACTION "C"

0.5 Moles of dihydromyrcenyl chloride having the structure:

is admixed with 80 ml water and 41 grams of potassium carbonate (0.3 moles). The resulting mixture is refluxed for a period of 9.5 hours. At the end of this period, less than 1% dihydromyrcenol having the structure:

was produced.

REACTION "D"

0.5 Moles of dihydromyrcenyl chloride having the structure:

is admixed with 80 ml water and 32 grams of sodium carbonate (0.3 moles). The resulting mixture is refluxed for a period of 9.5 hours. At the end of this 9.5 hour period, less than 4% of dihydromyrcenol having the structure:

was produced.

REACTION "E"

0.5 Moles of dihydromyrcenyl chloride having the structure:

is admixed with 80 ml water and 30 grams (0.3 moles) of calcium carbonate. The resulting mixture is refluxed for a period of 9.5 hours. At the end of the 9.5 hour period, the reaction mass contained 23% by weight of dihydromyrcenol having the structure:

REACTION "F"

0.5 Moles of dihydromycenyl chloride (95 grams) having the structure:

is admixed with 80 ml water and 50 grams (0.3 moles) of sodium bicarbonate. The resulting mixture is refluxed for a period o 9.5 hours. At the end of the 9.5 hour period, the reaction mass contained 8% by weight of dihydromyrcenol having the structure:

EXAMPLE IV

Preparation of Dihydromyrcenyl Acetate

Reaction:

Into a 1 liter reaction vessel equipped with reflux condenser, stirrer, thermometer and heating mantle are placed 400 grams (about 2 moles) of the mixture of tertiary chlorides produced according to Example II(A) having the structures:

97 grams (1.2 moles) of zinc oxide and 600 grams (10 moles) of acetic acid.

The resulting mixture is heated to 35° C. and maintained at a temperature in the range of 25°–35° C. for a period of 12 hours. At the end of the 12 hour period, the reaction product was distilled on a 12″ Goodloe column yielding the following fractions:

| FRACTION NO. | VAPOR TEMP. (°C.) | LIQUID TEMP. (°C.) | VACUUM PRESSURE mm/Hg. |
|---|---|---|---|
| 1 | 25/55 | 45/85 | 20/2 |
| 2 | 78 | 106 | 20 |
| 3 | 95 | 108 | 20 |
| 4 | 101 | 120 | 20 |
| 5 | 101 | 120 | 20 |
| 6 | 170 | 87 | 20 |
| 7 | 175 | 82 | 20 |

FIG. 4 is the GLC profile for the crude reaction product. The peak indicated by reference numeral 111 is the peak for the dihydromyrcenyl acetate having the structure:

What is claimed is:

1. A process for preparing dihydromyrcenol comprising the steps of:
   (i) hydrogenating α-pinene to form α-pinane;
   (ii) pyrolyzing the resulting α-pinane to form a mixture of hydrocarbons;
   (iii) reacting the resulting mixture of hydrocarbons with hydrogen chloride in the presence of an acid catalyst selected from the group consisting of Lewis acids and protonic acids thereby forming a mixture of tertiary chlorides;
   (iv) reacting the resulting mixture of tertiary chlorides with water in the presence of a hydroxylating catalyst having the structure:

$$M_P X_Q$$

wherein M represents an element selected from the group consisting of Zn, Ca, Mg, Mn and Co; wherein X represents 0 or an anion selected from the group consisting of halide, hydroxide, carbonate, bicarbonate, phosphate, monobasic acid phosphate and dibasic acid phosphate; and wherein P represents an integer of 1 or 3 and Q represents an integer of 1 or 2 with the provisos that when X is a trivalent anion, then P is 3 and Q is 2 and when X is a divalent anion or is 0, then P is 1 and Q is 1 and when X is a monovalent anion, then P is 1 and Q is 2 according to the reaction:

and (v) recovering dihydromyrcenol from the reaction mixture.

2. A process for forming dihydromyrcenyl acetate having the structure:

comprising the steps of:
(i) hydrogenating α-pinene to form α-pinane;
(ii) pyrolyzing the α-pinane to form a mixture of hydrocarbons;
(iii) reacting the resulting mixture of hydrocarbons with hydrogen chloride in the presence of an acid catalyst selected from the group consisting of Lewis acids and protonic acids in order to form a mixture of tertiary chlorides;
(iv) reacting the mixture of tertiary chlorides with acetic acid in the presence of a hydroxylating catalyst thereby forming a mixture containing a major proportion of dihydromyrcenyl acetate, the hydroxylating catalyst having the formula:

$$M_P X_Q$$

wherein M represents an element selected from the group consisting of Zn, Ca, Mg, Mn and Co; wherein X represents O or an anion selected from the group consisting of halide, hydroxide, carbonate, bicarbonate, phosphate, monobasic acid phosphate and dibasic acid phosphate; and wherein P represents an integer of 1 or 3 and Q represents an integer of 1 or 2 with the provisos that when X is a trivalent anion, then P is 3 and Q is 2 and when X is a divalent anion or is O, then P is 1 and Q is 1 and when X is a monovalent anion, then P is 1 and Q is 2 according to the reaction:

and (v) recovering the dihydromyrcenyl acetate from the reaction mixture.

3. A process for preparing dihyromycenol comprising the steps of:
(i) forming a mixture of hydrocarbons consisting essentially of hydrocarbons having the structures:

(ii) reacting the said mixture of hydrocarbons with hydrogen chloride in the presence of an acid catalyst selected from the group consisting of Lewis acids and protonic acids thereby forming a mixture of tertiary chlorides;

(iii) reacting the resulting mixture of tertiary chlorides with water in the presence of a hydroxylating catalyst having the structure:

$M_P X_Q$ wherein M represents an element selected from the group consisting of Zn, Ca, Mg, Mn and Co; wherein X represents 0 or an anion selected from the group consisting of halide, hydroxide, carbonate, bicarbonate, phosphate, monobasic acid phosphate and dibasic acid phosphate; and wherein P represents an integer of 1 or 3 and Q represents an integer of 1 or 2 with the provisos that when X is a trivalent anion then P is 3 and Q is 2 and when X is a divalent anion or is 0 then P is 1 and Q is 1 and when X is a monovalent anion then P is 1 and Q is 2 according to the reaction:

and (iv) recovering dihydromyrcenol from the reaction mixture.

4. A process for forming a dihydromyrcenyl acetate having the structure:

comprising the steps of:
(i) providing a mixture of hydrocarbons having the structures:

(ii) reacting the resulting mixture of hydrocarbons with hydrogen chloride in the presence of an acid catalyst selected from the group consisting of Lewis acids and protonic acids in order to form a mixture of tertiary chlorides;

(iii) reacting the mixture of tertiary chlorides with acetic acid in the presence of a hydroxylating catalyst thereby forming a mixture containing a major proportion of dihydromyrcenyl acetate, the hydroxylating catalyst having the formula:

$M_P X_Q$ wherein M represents an element selected from the group consisting of Zn, Ca, Mg, Mn and Co; wherein X represents 0 or an anion selected from the group consisting of halide, hydroxide, carbonate, bicarbonate, phosphate, monobasic acid phosphate and dibasic acid phosphate; and wherein P represents an integer of 1 or 3 and Q represents an integer of 1 or 2 with the provisos that when X is a trivalent anion, then P is 3 and Q is 2 and when X is a divalent anion or is 0, then P is 1 and Q is 1 and when X is a monovalent anion, then P is 1 and Q is 2 according to the reaction:

and
(iv) recovering the dihydromyrcenyl acetate from the reaction mixture.

* * * * *